(12) United States Patent
Shimakawa et al.

(10) Patent No.: US 8,183,407 B2
(45) Date of Patent: May 22, 2012

(54) PROCESS FOR PRODUCTION OF ISOCYANATE, ISOCYANATE PRODUCED BY THE PROCESS, AND USE OF THE ISOCYANATE

(75) Inventors: Chitoshi Shimakawa, Arao (JP);
Hiroyuki Morijiri, Yokohama (JP);
Hidetoshi Hayashi, Omuta (JP);
Norihiko Fukatsu, Omuta (JP); Seiichi Kobayashi, Omuta (JP); Homare Yumoto, Omuta (JP); Junichi Ishiyama, Omuta (JP); Shinya Tsuchiyama, Arao (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 0 days.

(21) Appl. No.: 11/988,490

(22) PCT Filed: Jul. 20, 2006

(86) PCT No.: PCT/JP2006/314417
§ 371 (c)(1),
(2), (4) Date: Jan. 6, 2009

(87) PCT Pub. No.: WO2007/010996
PCT Pub. Date: Jan. 25, 2007

(65) Prior Publication Data
US 2009/0124785 A1 May 14, 2009

(30) Foreign Application Priority Data
Jul. 22, 2005 (JP) ................................. 2005-213148

(51) Int. Cl.
*C07C 291/00* (2006.01)
(52) U.S. Cl. ...................................................... 560/347
(58) Field of Classification Search .................. 560/347; 528/44
See application file for complete search history.

(56) References Cited

U.S. PATENT DOCUMENTS

| 2,642,449 A | 6/1953 | Morningstar et al. | |
| 4,922,005 A * | 5/1990 | Ajioka et al. | 560/347 |
| 5,523,467 A * | 6/1996 | Okazaki et al. | 560/347 |
| 5,693,738 A * | 12/1997 | Okazaki et al. | 528/51 |
| 2006/0155093 A1 | 7/2006 | Kitahara | |

FOREIGN PATENT DOCUMENTS

| CN | 1614134 A | 5/2005 |
| EP | 0 384 463 A | 8/1990 |
| EP | 0 424 836 A | 5/1991 |
| EP | 0 850 985 A | 7/1998 |
| GB | 1086782 | 10/1967 |
| GB | 1146664 | 3/1969 |
| JP | 50-108239 A | 8/1975 |
| JP | 07-233137 A | 9/1995 |
| JP | 07-309827 A | 11/1995 |
| JP | 11-310567 A | 11/1999 |
| JP | 2003-043201 A | 2/2003 |
| JP | 2003-286241 A | 10/2003 |
| JP | 2004-244377 A | 9/2004 |
| WO | WO 2004/108786 A1 | 12/2004 |

OTHER PUBLICATIONS

Search Report issued in corresponding Chinese Patent Application No. 2006800221703 dated Jan. 22, 2010 with partial English Translation.
Ken Terao, et al: "Solvent and Temperature Effects on the Chiral Aggregation of Optically Active Poly(dialkylsilane)s Confined in Microcapsules", LANGMUIR (2004), 20(2), 306-308 CODEN: LANGD5; ISSN: 0743-7463, 2004.
"Indirect food additives; polymers, bis(isocyanatomethyl)benzene and bis(isocyanatomethyl)cyclohexane" Federal Register (1981), 46(224), 57033-4, Nov. 20, 1981 CODEN: FEREAC; ISSN: 0097-6326,1981.
Extended European Search Report issued in corresponding European Patent Application No. 06 78 1372 dated Apr. 26, 2010.

* cited by examiner

*Primary Examiner* — Milton I Cano
*Assistant Examiner* — Michael L Leonard
(74) *Attorney, Agent, or Firm* — Buchanan Ingersoll & Rooney PC

(57) ABSTRACT

An isocyanate has been widely used as a starting material for the production of a polyurethane material, a polyisocyanurate material or the like which is suitably applicable to the field of optical materials. Disclosed is a process for producing an isocyanate which includes a step for producing the isocyanate in the form of a hydrochloride with improved productivity. A process for producing a linear or cyclic aliphatic isocyanate comprising the step of reacting a linear or cyclic aliphatic amine with hydrogen chloride to yield a hydrochloride of the linear or cyclic aliphatic amine, the step being performed under a pressure higher by 0.01 MPa or more than the atmospheric pressure.

11 Claims, No Drawings

PROCESS FOR PRODUCTION OF ISOCYANATE, ISOCYANATE PRODUCED BY THE PROCESS, AND USE OF THE ISOCYANATE

TECHNICAL FIELD

The present invention relates to a process for producing a linear or cyclic aliphatic isocyanate comprising a step of reacting a linear or cyclic aliphatic amine with hydrogen chloride (step for obtaining hydrochloride). The present invention further relates to a linear or cyclic aliphatic isocyanate obtained by the production process and the use of the isocyanate.

BACKGROUND ART

An isocyanate compound is useful as a raw material for the production of a polyurethane material, a polyurea material, a polyisocyanurate material and the like used in the fields of chemical, resin and paint industries.

In particular, since a plastic lens using a polyurethane material containing a sulfur atom or the like is lightweight and hardly broken as compared to an inorganic lens, and can be dyed, in late years, it has quickly come into wide use as an optical element of a spectacle lens, a camera lens and the like.

In processes for preparing important isocyanates in the various applications including a raw material of resin for the aforementioned plastic lens, further rationalization of such processes has been in demand. So, various proposals have already been made.

As the process for preparing isocyanates, a phosgene process comprising reacting a raw material amine with phosgene can be cited as a typical example. As the phosgene process, a direct process comprising directly reacting a raw material amine with phosgene, and a hydrochloride process comprising converting a raw material amine into hydrochloride and then reacting with phosgene have been widely known.

The direct process is much simpler as compared to the hydrochloride process, but urea has been generated as a by-product by reacting carbamoyl chloride or isocyanate that is an intermediate with a raw material amine in many cases. In case of the preparation of an aromatic isocyanate, since urea generated as a by-product is further reacted with phosgene to generate an isocyanate, products is obtained in relatively high yield and generation of urea is not usually a problem accordingly. However, when a linear or cyclic aliphatic amine is reacted with phosgene in the direct process, since the byproduced urea is reacted with phosgene, there has been known that a chlorine derivative is generated as a by-product (for example, refer to Patent Document 1). The chlorine derivative is usually byproduced in an amount of 3 to 10% and is sometimes byproduced as high as 20%. Hence the yield of the desired product might be decreased and the physical properties of the resin such as urethane or the like in use might be also adversely affected. So, the direct process is not usually adopted. Namely, in case of the preparation of a linear or cyclic aliphatic isocyanate, in order to suppress generation of urea as a by-product, the hydrochloride process comprising converting a raw material amine into hydrochloride and then reacting with phosgene to prepare an isocyanate has been employed (for example, refer to Patent Documents 2 to 5).

Of these Patent Documents, in Patent Document 3 to 5, there have been described processes comprising preparing an isocyanate by converting a raw material amine into hydrochloride in an organic solvent or the like in advance and then reacting with phosgene.

Patent Document 1: GB Patent No. 1086782
Patent Document 2: Japanese Patent Laid-open No. 1975-108239
Patent Document 3: Japanese Patent Laid-open No. 1999-310567
Patent Document 4: GB Patent No. 1146664
Patent Document 5: Japanese Patent Laid-open No. 2003-286241

DISCLOSURE OF THE INVENTION

However, in the hydrochloride process, the increased viscosity of the obtained hydrochloride slurry is accompanied by disadvantages of a decrease of the productivity and the like. So, it has been demanded to be solved. For example, in the hydrochloride process, generally used is a process which comprises blowing hydrogen chloride gas into an organic solvent with a raw material amine dissolved therein for the production of hydrochloride. At this time, the concentration of the raw material amine is, for example, not less than 5 weight %, which is industrially favorable. When the raw material amine is reacted with hydrogen chloride gas under a condition such a concentration, as the reaction is progressed, the viscosity of the hydrochloride slurry is increased, for example, to 5,000 to 10,000 mPa·s, the fluidity of the hydrochloride slurry is decreased, and it is difficult to transfer the hydrochloride by a pump or the like in some cases. A decrease of the productivity caused by the difficulties in transferring the liquid becomes particularly important when continuously carrying out the halogenation.

In order to solve the above objects, the present inventors have conducted an extensive study and as a result, have found that the pressure at the time of the production of a hydrochloride of a linear or cyclic aliphatic amine is higher by 0.01 MPa or more than the atmospheric pressure, whereby it is possible to lower the viscosity of the hydrochloride slurry. Thus, the present invention has been completed. If the fluidity is enhanced by the lowered viscosity of the hydrochloride slurry, a hydrochloride having an excellent liquid transfer property is obtained, which is particularly useful for the improvement of the productivity of the hydrochloride (particularly the improvement of the productivity when the reaction for obtaining hydrochloride is continuously conducted).

Furthermore, it was found that the pressure at the time of the production of a hydrochloride of a linear or cyclic aliphatic amine is in the aforementioned condition, whereby the increase of the particle diameter of the hydrochloride particle in the hydrochloride slurry can be suppressed and the increase of the viscosity of the hydrochloride slurry can be suppressed. It was also found that the yield of isocyanate is increased through the improvement of the conversion rate of hydrochloride at the phosgenation in some cases.

That is, the present invention relates to (1) a process for producing a linear or cyclic aliphatic isocyanate comprising a step of reacting a linear or cyclic aliphatic amine with hydrogen chloride to yield a hydrochloride of the linear or cyclic aliphatic amine, wherein said step is performed under a pressure higher by 0.01 MPa or more than the atmospheric pressure.

The following (2) to (11) are each one of preferred embodiments of the present invention:

(2) the process for producing a linear or cyclic aliphatic isocyanate as set forth in (1), wherein said linear or cyclic aliphatic amine is a di- or higher functional linear or cyclic aliphatic amine;

(3) the process for producing a linear or cyclic aliphatic isocyanate as set forth in (1), wherein said step is a step of reacting a di- or higher functional linear or cyclic aliphatic amine with hydrogen chloride in an organic solvent in a tank reactor;

(4) the process for producing a linear or cyclic aliphatic isocyanate as set forth in (1), wherein said step is a step of reacting a di- or higher functional linear or cyclic aliphatic amine in an organic solvent with hydrogen chloride blown into the organic solvent;

(5) the process for producing a linear or cyclic aliphatic isocyanate as set forth in any one of (1) to (4), wherein the viscosity of a slurry containing the hydrochloride of the linear or cyclic aliphatic amine obtained in said step measured at 120 degree centigrade using a Brookfield LVT viscometer is not more than 2,000 mPa·s;

(6) the process for producing a linear or cyclic aliphatic isocyanate as set forth in any one of (1) to (4), wherein said step is performed under a pressure higher by the range of 0.01 MPa or more and 1.0 MPa or less than the atmospheric pressure;

(7) the process for producing a linear or cyclic aliphatic isocyanate as set forth in any one of (1) to (4), wherein the reaction temperature in said step is not less than −20 degree centigrade and not more than 180 degree centigrade;

(8) the process for producing a linear or cyclic aliphatic isocyanate as set forth in any one of (1) to (4), wherein at least one kind of organic aromatic solvent is used in said step;

(9) the process for producing a linear or cyclic aliphatic isocyanate as set forth in any one of (2) to (4), wherein said di- or higher functional linear or cyclic aliphatic amine is a compound having a primary amino group;

(10) the process for producing a linear or cyclic aliphatic isocyanate as set forth in any one of (2) to (4), wherein said di- or higher functional linear or cyclic aliphatic isocyanate is one or more compounds selected from xylylene diisocyanate, bis(isocyanatomethyl)norbornene, hexamethylene diisocyanate and bis(isocyanatomethyl)cyclohexane; and

(11) the process for producing a linear or cyclic aliphatic isocyanate as set forth in any one of (1) to (4), wherein the total amine concentration in the reaction system is not less than 5 weight % and not more than 40 weight % in said step.

The present invention relates to (12) a linear or cyclic aliphatic isocyanate produced by the process as set forth in any one of (1) to (11).

The present invention relates to (13) a polyurethane resin produced by using the linear or cyclic aliphatic isocyanate as set forth in (12).

The present invention relates to (14) a lens containing the polyurethane resin as set forth in (13).

Furthermore, the present invention relates to (15) a process for producing a hydrochloride of a linear or cyclic aliphatic amine, which comprises reacting a linear or cyclic aliphatic amine with hydrogen chloride under a pressure higher by 0.01 MPa or more than the atmospheric pressure.

The following (16) to (18) are each one of preferred embodiments in the process for producing a hydrochloride of a linear or cyclic aliphatic amine of the present invention:

(16) the process for producing a hydrochloride of a linear or cyclic aliphatic amine as set forth in (15), wherein said linear or cyclic aliphatic amine is a di- or higher functional linear or cyclic aliphatic amine;

(17) the process for producing a hydrochloride of a linear or cyclic aliphatic amine as set forth in (15), which comprises reacting a di- or higher functional linear or cyclic aliphatic amine with hydrogen chloride in an organic solvent in a tank reactor; and

(18) the process for producing a hydrochloride of a linear or cyclic aliphatic amine as set forth in (15), which comprises reacting a di- or higher functional linear or cyclic aliphatic amine in an organic solvent with hydrogen chloride blown into the organic solvent.

According to the present invention, the pressure at the time of producing a hydrochloride of a linear or cyclic aliphatic amine is higher by 0.01 MPa or more than the atmospheric pressure, whereby it becomes possible to lower the viscosity of the obtained hydrochloride slurry of the linear or cyclic aliphatic amine. Due to this, the fluidity and liquid transfer property of the hydrochloride slurry are enhanced and it is possible to produce a hydrochloride having excellent liquid transfer property which is particularly suitably applicable to the continuous reaction for obtaining hydrochloride. So, the productivity of the hydrochloride is improved.

BEST MODE FOR CARRYING OUT THE INVENTION

The present invention will be illustrated in detail below.

The process for producing a linear or cyclic aliphatic isocyanate of the present invention includes a step of reacting a linear or cyclic aliphatic amine with hydrogen chloride to yield a slurry containing a hydrochloride of a linear or cyclic aliphatic amine (hereinafter referred to as "reaction step for obtaining hydrochloride"). Furthermore, to produce the aforementioned isocyanate, a step of reacting the amine hydrochloride obtained by the aforementioned step with phosgene (hereinafter referred to as "phosgenation step") is involved, whereby the amine hydrochloride is phosgenated to produce an isocyanate.

Reaction Step for Obtaining Hydrochloride

In the present invention, the reaction for obtaining hydrochloride is carried out in a reactor under a pressure higher by 0.01 MPa or more than the atmospheric pressure, preferably 0.02 MPa or more, and more preferably 0.03 MPa or more. Due to this, the viscosity of the hydrochloride slurry obtained in the reaction for obtaining hydrochloride can be lowered, preferably to not more than 2,000 mPa·s. Incidentally, the viscosity of the slurry is a value measured at 120 degree centigrade by using a Brookfield LVT viscometer.

According to the production process of the present invention comprising carrying out the reaction for obtaining hydrochloride under such a pressure, the fluidity and liquid transfer property are improved because of the lowered viscosity of the hydrochloride slurry, while a hydrochloride having excellent liquid transfer property which is particularly suitably applicable to the continuous reaction for obtaining hydrochloride can be produced. Accordingly, the productivity of the hydrochloride can be improved.

Furthermore, according to the production process of the present invention, since the viscosity of the hydrochloride slurry is in the above range, an unreacted raw material amine and a chlorine derivative generated from the unreacted raw material amine can be decreased in some cases because of the improvement of the mixing efficiency of the hydrochloride slurry. As a result, the conversion rate of the raw material amine in the reaction for obtaining hydrochloride is improved, and the yield of isocyanate is improved, and the like in some cases. Furthermore, according to the production process of the present invention, the increase of the particle diameter of the hydrochloride particle contained in the hydrochloride slurry can be suppressed and the hydrochloride particle can be finer in some cases. Due to this, the increase of the viscosity of the hydrochloride slurry can be suppressed, and the yield of the isocyanate can be improved through the improvement of the conversion rate of hydrochloride at the phosgenation in some cases.

In the present invention, the aforementioned linear or cyclic aliphatic amine is preferably a di- or higher functional linear or cyclic aliphatic amine. When the aforementioned linear or cyclic aliphatic amine is a di- or higher functional linear or cyclic aliphatic amine, a hydrochloride of a di- or higher functional linear or cyclic aliphatic amine can be obtained by the reaction for obtaining hydrochloride. Furthermore, the hydrochloride is phosgenated, whereby a di- or higher functional linear or cyclic aliphatic isocyanate can be obtained. The di- or higher functional linear or cyclic aliphatic isocyanate is reacted with a compound having two or more active hydrogen containing groups, whereby a polymer compound such as polyurethane or the like can be obtained. Thus, it is of practically high value.

Furthermore, in the present invention, the aforementioned reaction step for obtaining hydrochloride is preferably carried out in an organic solvent from the viewpoints of the stability of the reaction, the solubility of each component contributing to the reaction, and the like.

In the present invention, the reactor used for the aforementioned reaction step for obtaining hydrochloride is preferably a tank reactor, and particularly a tank reactor equipped with a stirrer for stirring the inside. In the present invention, a tank reactor refers to a reactor equipped with a reaction vessel in which at least a part of a substance (reaction product, generated product, solvent or the like) involved in the reaction is present in a liquid phase thereinside, and a reactor satisfying the relationship of $D1/D2 \leq 0.85$ when a diameter of a stirring blade is $D1$ and an internal diameter of the reaction vessel is $D2$. Furthermore, in the tank reactor used in the present invention, the ratio (D/L) of the bath diameter (D) and the bath length (L) is preferably not less than 0.1 and not more than 5.0. When D/L is not less than 0.1, hydrogen chloride gas can be well removed so that a phenomenon of the obtained hydrochloride exhibiting a whip shape for deteriorating the fluidity can be effectively suppressed. When D/L is not more than 5.0, it is easy to stir uniformly. As the result, the problem which unreacted amine is increased and the like can be effectively suppressed. From the viewpoint of a balance of such effects, the reactor having the aforementioned ratio of D/L of not less than 0.5 and not more than 1.5 is further desirable.

The reaction for obtaining hydrochloride can be carried out in various processes such as a process comprising introducing an organic solvent, preferably an organic aromatic solvent in a tank reactor, subjecting to a temperature elevation to a prescribed temperature and then adding a solvent with amine dissolved therein dropwise thereto and at the same time feeding hydrogen chloride gas, a process comprising heating the introduced solvent to a prescribed temperature, absorbing hydrogen chloride gas in advance and then adding an amine dissolved solution dropwise thereto and at the same time feeding hydrogen chloride gas, a process comprising heating a solvent with amine dissolved therein to a prescribed temperature and then feeding hydrogen chloride gas, or the like. The reaction for obtaining hydrochloride is preferably carried out in any of the above-cited processes. However, the reaction for obtaining hydrochloride carried out in processes other than the cited processes is not excluded. In any of these processes, when hydrogen chloride gas is inserted, it is preferable that hydrogen chloride gas is blown into the organic solvent from the viewpoint of the reaction efficiency.

The pressure in a tank reactor for carrying out the reaction for obtaining hydrochloride of the present invention is higher by 0.01 MPa or more than the atmospheric pressure from the viewpoint that the viscosity of the hydrochloride slurry obtained in the reaction for obtaining hydrochloride is preferably not more than 2,000 mPa·s or the conversion rate of the raw material amine is preferably not less than 99 mole %. The pressure is more preferably higher by 0.02 MPa or more than the atmospheric pressure. The pressure is further preferably higher by 0.03 MPa or more than the atmospheric pressure.

On the other hand, when the reaction for obtaining hydrochloride is carried out under the atmospheric pressure, the particle diameter of the hydrochloride particle in the hydrochloride slurry becomes large or the viscosity of the hydrochloride slurry is increased so that the decrease of the mixing efficiency in the reactor is resulted due to the decrease of the liquid transfer property or the fluidity. For that reason, the increase of unreacted amine or the increase of chloride generated in the reaction with phosgene might be resulted in some cases.

In the present invention, when the upper limit of the pressure at the reaction for obtaining hydrochloride is higher by 1.0 MPa or less than the atmospheric pressure, it is preferable that the solubility of hydrogen chloride gas in the hydrochloride slurry is increased so that the reaction speed at the reaction for obtaining hydrochloride is enhanced. Furthermore, since the fluidity is improved, the liquid transfer property of the hydrochloride slurry preferably becomes excellent as well. The pressure condition is more preferably 0.5 MPa or less than the atmospheric pressure, and further preferably 0.3 MPa or less than the atmospheric pressure. When the pressure in the reactor for obtaining hydrochloride is extremely high, there occur some problems such that release of hydrogen chloride gas becomes worse, the hydrochloride slurry exhibits a whip shape, and the fluidity is adversely deteriorated in some cases.

Incidentally, the lower limit and upper limit of the pressure at the reaction for obtaining hydrochloride can be in any combination. In the present invention, from the viewpoints of the above effects, the reaction for obtaining hydrochloride is preferably carried out under a pressure higher by not less than 0.01 MPa and not more than 1.0 MPa than the atmospheric pressure, and more preferably carried out under a pressure higher by not less than 0.01 MPa and not more than 0.5 MPa than the atmospheric pressure.

According to the production process of the present invention, the conversion rate of the raw material amine can be not less than 99 mole % in some cases. When the conversion rate of the raw material amine is not less than 99 mole %, it is preferable that the yield of isocyanate is high and the influence of the by-product can be suppressed.

The conversion rate of the raw material amine is measured in the following manner. The amine remained in the slurry after the completion of the reaction for obtaining hydrochloride is subjected to neutralization titration to calculate the mole number of the remained amine. From the mole number of the remained amine and the mole number of the introduced amine, the amine conversion rate is calculated according to the following formula.

Formula: Amine conversion rate=((mole number of introduced amine−mole number of remained amine)/mole number of introduced amine)×100

The total amine concentration in the present invention is preferably not less than 5 weight % and not more than 40 weight % in consideration of the industrial production efficiency. The total amine concentration is a value calculated by dividing the amount of amine introduced into the reactor for obtaining hydrochloride by the total weight of the raw material introduced into the reactor for obtaining hydrochloride.

When the concentration is not less than 5 weight %, it is preferable that the production efficiency is high. When the concentration is not more than 40 weight %, problems of the deteriorated fluidity of the hydrochloride slurry, the reduced mixing efficiency due to the increase of the slurry viscosity, increased unreacted amine, decreased liquid transfer property, increased chloride at the reaction with phosgene and the like can be effectively suppressed. For that reason, the total amine concentration is preferably not less than 5 weight % and not more than 35 weight %, and more preferably not less than 5 weight % and not more than 30 weight %.

The temperature at the reaction for obtaining hydrochloride in the present invention is preferably not less than −20 degree centigrade and not more than 180 degree centigrade in consideration of the decrease of unreacted amine, prevention of a chlorine derivative generated as a by-product derived from the unreacted amine, fine particle diameter of generated hydrochloride, thermal balance at the time of shifting to the next reaction with phosgene or the like.

When the temperature is not less than −20 degree centigrade, phenomena such that condensation of the hydrochloride particle is difficult and hydrochloride in the bulk state at the halogenation is generated can be effectively suppressed. When the temperature is not more than 180 degree centigrade, phenomena such that the generated hydrochloride exhibits a whip shape, the fluidity is damaged and it is difficult to transfer hydrochloride can be effectively suppressed. The temperature at the reaction for obtaining hydrochloride is preferably not less than −20 degree centigrade and not more than 180 degree centigrade, more preferably not less than 60 degree centigrade and not more than 175 degree centigrade, and further preferably not less than 100 degree centigrade and not more than 170 degree centigrade.

Phosgenation Step

The reaction of a hydrochloride obtained by the reaction for obtaining hydrochloride with phosgene can also be carried out under a normal pressure or a pressure, but the phosgenation is preferably carried out under a normal pressure from the viewpoint of suppression of side reaction due to byproduced hydrogen chloride gas. Moreover, the temperature of the reaction with phosgene is not less than 120 degree centigrade and not more than 180 degree centigrade, preferably not less than 130 degree centigrade and not more than 175 degree centigrade, and further preferably not less than 150 degree centigrade and not more than 170 degree centigrade from the viewpoints of the reaction speed and suppression of converting generated isocyanate into tar.

In the present invention, as the equivalent ratio of amine and hydrogen chloride gas at the reaction for obtaining hydrochloride, hydrogen chloride gas is not less than 1.0 and not more than 2.5 and preferably not less than 1.1 and not more than 2.0 based on 1.0 of amine. When it is not less than 1.0, the conversion rate of the raw material amine can be maintained high. When it is not more than 2.5, it is industrially more favorable from the viewpoint of the economical efficiency.

The di- or higher linear or cyclic aliphatic amine which is preferably used in the present invention is not particularly limited, but typical examples thereof include linear aliphatic amines such as hexamethylene diamine, 2,2-dimethylpentane diamine, 2,2,4-trimethylhexane diamine, butene diamine, 1,3-butadiene-1,4-diamine, 2,4,4-trimethylhexamethylene diamine, 1,6,11-undecane triamine, 1,3,6-hexamethylene triamine, 1,8-diisocyanato-4-isocyanatomethyloctane, bis(aminoethyl)carbonate, bis(aminoethyl)ether, lysine diamino methyl ester, lysine triamine, xylylene diamine, bis(aminoethyl)benzene, bis(aminopropyl)benzene, α,α,α',α'-tetramethylxylylene diamine, bis(aminobutyl)benzene, bis(aminomethyl)naphthalene, bis(aminomethyl)diphenyl ether, bis(aminoethyl)phthalate, mesitylylene triamine, 2,6-di(aminomethyl)furan and the like;

cyclic aliphatic amines such as bis(aminomethyl)cyclohexane, dicyclohexylmethane diamine, cyclohexane diamine, methylcyclohexane diamine, dicyclohexyldimethylmethane diamine, 2,2-dimethyl dicyclohexylmethane diamine, 2,5-bis(aminomethyl)bicyclo-[2,2,1]-heptane, 2,6-bis(aminomethyl)bicyclo-[2,2,1]-heptane, 3,8-bis(aminomethyl)tricyclodecane, 3,9-bis(aminomethyl)tricyclodecane, 4,8-bis(aminomethyl)tricyclodecane, 4,9-bis(aminomethyl)tricyclodecane, bis(aminomethyl)norbornene and the like; and sulfur-containing linear aliphatic amines such as bis(aminomethyl)sulfide, bis(aminoethyl)sulfide, bis(aminopropyl)sulfide, bis(aminohexyl)sulfide, bis(aminomethyl)sulfone, bis(aminomethyl)disulfide, bis(aminoethyl)disulfide, bis(aminopropyl)disulfide, bis(aminomethylthio)methane, bis(aminoethylthio)methane, bis(aminoethylthio)ethane, bis(aminomethylthio)ethane, 1,5-diamino-2-aminomethyl-3-thiapentane and the like.

Isocyanate obtained by reacting the amine hydrochloride obtained in the aforementioned reaction for obtaining hydrochloride with phosgene is not particularly limited, but typical examples thereof include linear aliphatic polyisocyanate such as hexamethylene diisocyanate, 2,2-dimethylpentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanatomethyloctane, bis(isocyanatoethyl)carbonate, bis(isocyanatoethyl)ether, lysine diisocyanatomethyl ester, lysine triisocyanate, xylylene diisocyanate, bis(isocyanatoethyl)benzene, bis(isocyanatopropyl)benzene, α,α,α',α'-tetramethylxylylene diisocyanate, bis(isocyanatobutyl)benzene, bis(isocyanatomethyl)naphthalene, bis(isocyanatomethyl)diphenyl ether, bis(isocyanatoethyl)phthalate, mesitylylene triisocyanate, 2,6-di(isocyanatomethyl)furan and the like;

cyclic aliphatic polyisocyanate such as bis(isocyanatomethyl)cyclohexane, dicyclohexylmethane diisocyanate, cyclohexane diisocyanate, methylcyclohexane diisocyanate, dicyclohexyl dimethylmethane diisocyanate, 2,2-dimethyldicyclohexylmethane diisocyanate, 2,5-bis(isocyanatomethyl)bicyclo-[2,2,1]-heptane, 2,6-bis(isocyanatomethyl)bicyclo-[2,2,1]-heptane, 3,8-bis(isocyanatomethyl)tricyclodecane, 3,9-bis(isocyanatomethyl)tricyclodecane, 4,8-bis(isocyanatomethyl)tricyclodecane, 4,9-bis(isocyanatomethyl)tricyclodecane, bis(isocyanatomethyl)norbornene and the like; and sulfur-containing linear aliphatic isocyanate such as bis(isocyanatomethyl)sulfide, bis(isocyanatoethyl)sulfide, bis(isocyanatopropyl)sulfide, bis(isocyanatohexyl)sulfide, bis(isocyanatomethyl)sulfone, bis(isocyanatomethyl)disulfide, bis(isocyanatoethyl)disulfide, bis(isocyanatopropyl)disulfide, bis(isocyanatomethylthio)methane, bis(isocyanatoethylthio)methane, bis(isocyanatoethylthio)ethane, bis(isocyanatomethylthio)ethane, 1,5-diisocyanato-2-isocyanatomethyl-3-thiapentane and the like.

Particularly preferable examples of the compound for various applications of optical components among the above-cited compounds obtained by the production process of the present invention include xylylene diisocyanate, bis(isocyanatomethyl)norbornene, hexamethylene diisocyanate and bis(isocyanatomethyl)cyclohexane.

The solvent used in the present invention is not particularly limited. However, it is preferable to use an organic aromatic compound with a high boiling point in which the hydrochloric acid solubility at the reaction for obtaining hydrochloride is high, the phosgene solubility at the phosgenation is high, and the hydrochloric acid solubility is small. Typical examples of the organic aromatic compound include, though not restricted to, 1,2-diethylbenzene, 1,3-diethylbenzene, 1,4-diethylbenzene, isopropylbenzene, 1,2,4-trimethylbenzene, amylbenzene, diamylbenzene, triamylbenzene, dodecylbenzene, p-cymene, cumene, dimethyl phthalate, diethyl phthalate, dibutyl phthalate, di-2-ethylhexyl phthalate, methyl benzoate, ethyl benzoate, butyl benzoate, propyl benzoate, isoamyl benzoate, benzyl benzoate, methyl salicylate, methylphenyl ether, ethylphenyl ether, diisoamyl ether, n-hexyl ether, orthodichlorobenzene, p-chlorotoluene, bromobenzene, 1,2,4-trichlorobenzene and the like. Of the exemplified solvents, particularly preferably used for carrying out the present invention is an aromatic halogen compound.

An isocyanate has been widely used in various industrial fields including optical materials. The process for producing an isocyanate of the present invention is capable of enhancing its production efficiency and has a technically and industrially high value.

The isocyanate compound obtained by the production process of the present invention is excellent in the economical efficiency, and it is easy to reduce the unreacted raw material amine and a chorine derivative generated from the unreacted raw material amine. For that reason, by using the isocyanate compound, resins or optical products excellent in quality can be obtained with high economical efficiency.

The isocyanate compound obtained by the production process of the present invention is useful as a raw material for the production of various resins such as a polyurethane resin (including a polythiourethane resin), a polyurea resin, a polyisocyanurate resin and the like. Since a chlorine derivative highly needs to be removed to produce the polyurethane resin, the isocyanate compound obtained by the production process of the present invention is particularly useful as a raw material for the production of a polyurethane resin. That is, the isocyanate obtained by the present invention is excellent in the economical efficiency, and it is easy to reduce the unreacted raw material amine and a chorine derivative generated from the unreacted raw material amine. By using such an isocyanate, resins such as a polyurethane resin or the like and products such as lens or the like excellent in quality can be obtained with high economical efficiency.

A process for producing a polyurethane resin from the isocyanate compound and conditions (kind of isocyanate compounds, kind of compounds reacting with an isocyanate resin, kind of catalysts, kind of other additives, amount ratio thereof, reaction temperature, reaction time and the like) are not particularly limited. Conventional processes and conditions known in the art can be properly used in the ranges in which the object of the present invention is not impaired. For example, those described in Japanese Patent Laid-open No. 2003-043201 can be preferably used.

Since molded articles composed of the polyurethane resin obtained as described above have excellent impact resistance and dye-affinity, and high transparency in many cases, such articles are particularly suitable as materials of plastic lenses. Plastic lenses using the polyurethane materials are particularly useful as optical components of spectacle lenses, camera lenses and the like.

EXAMPLES

The present invention is now illustrated in detail below with reference to Examples. However, the range of the present invention is not restricted to these Examples in any sense.

Incidentally, the following Examples and Comparative Examples were measured in the following manner.

(Conversion Rate of Amine)

Amine remained in the slurry after the completion of the reaction for obtaining hydrochloride was subjected to neutralization titration to calculate the mole number of the remained amine. From the mole number of the remained amine and the mole number of the introduced amine, the conversion rate was calculated according to the following formula.

Formula: Amine conversion rate=((mole number of introduced amine−mole number of remained amine)/mole number of introduced amine)×100

(Generation Rate of Chloride)

The reaction solution after the completion of the reaction with phosgene was analyzed by gas chromatography to calculate the mole number of chloride. The mole number of chloride was divided by the mole number of the introduced hydrochloride to calculate the generation rate.

(Purity of Isocyanate)

The finally obtained isocyanate was analyzed by gas chromatography to calculate the purity of the isocyanate.

(Conversion Rate of Hydrochloride)

A residue of the reaction filtrate obtained by filtering after the reaction with phosgene was subjected to neutralization titration to calculate the mole number of the remained hydrochloride. From the mole number of the remained hydrochloride and the mole number of the introduced hydrochloride, the conversion rate was calculated according to the following formula.

Formula: Hydrochloride conversion rate=((mole number of introduced hydrochloride−mole number of remained hydrochloride)/mole number of introduced hydrochloride)×100

(Method for Measurement of Hydrochloride Viscosity)

The slurry after the completion of the reaction for obtaining hydrochloride was weighed in a vessel and the measurement temperature was elevated to 120 degree centigrade. When the temperature reached 120 degree centigrade, the viscosity was measured with No. 2 rotor of a Brookfield LVT viscometer and the indication value was multiplied by a coefficient to calculate the viscosity.

(Method for Measurement of Particle Diameter)

A small amount of the slurry after the completion of the reaction for obtaining hydrochloride was picked out and measured by using SALD-2100, a laser diffraction particle size analyzer, manufactured by Shimadzu Corporation in an acetonitrile solvent. The measured particle diameter was a number average value of the total particle diameter.

Example 1

An autoclave (reactor) equipped with a reflux condenser, a stirring blade, a thermometer, a hydrogen chloride gas inlet tube, a phosgene inlet tube, a raw material bath, a raw material feeding pump and a pressure regulator was used. In the reactor, a value of a diameter of the stirring blade (D1)/an internal diameter of the reaction vessel (D2) was 0.7, a value of the bath diameter (D)/the bath length (L) was 0.59, and an inner volume of the reaction vessel was 2 L. To the reactor was fed 846 g of orthodichlorobenzene as a reaction solvent, and to the raw material bath were fed 136.2 g (1.0 mole) of m-xylylene diamine and 621 g of orthodichlorobenzene (total amine concentration: 8.5 weight %). Next, the temperature in the reactor was elevated to 120 degree centigrade and then the internal pressure was regulated by 0.01 MPa higher than the atmospheric pressure. Hydrogen chloride gas started to be fed into the reactor at a rate of 43.8 g/hr from the hydrogen chloride gas inlet tube and m-xylylene diamine diluted with a solvent simultaneously started to be fed at a rate of 379 g/hr from the raw material bath by using the raw material feeding pump. The total amount was fed over 2 hours. Furthermore, hydrogen chloride gas was fed at a rate of 20 g/hr and matured for 1 hour. After the completion of the reaction, the conversion rate of the raw material amine was calculated by the neutralization titrimetric method and as a result, the conversion rate was 99.80 mole %. Further, the viscosity of the obtained hydrochloride slurry was measured at 120 degree centigrade using a Brookfield LVT viscometer and as a result, it was 201 mPa·s. So, the slurry had sufficient fluidity. Moreover, a particle diameter of the hydrochloride particle was measured by using SALD-2100, a laser diffraction particle size analyzer, manufactured by Shimadzu Corporation in an acetonitrile solvent and as a result, the number average particle diameter of the hydrochloride particle was 25 μm. The obtained hydrochloride slurry was in a liquid phase and excellent in the fluidity. So, it was confirmed that when the hydrochloride was transferred to the next step, the hydrochloride did not remain in the reactor and the liquid transfer property was excellent accordingly.

Subsequently, the hydrochloride slurry in the reactor was heated to 160 degree centigrade and then phosgene was blown at a rate of 100 g/hr (1.0 mole/hr) from the phosgene inlet tube. The reaction was carried out for 8 hours while maintaining the temperature. After the completion of the reaction, nitrogen in the system was purged to remove unreacted phosgene and hydrogen chloride gas. The reaction solution was filtered to remove 0.8 g (dry weight) of unreacted hydrochloride. The obtained filtrate was desolvated to obtain 188.58 g (purity conversion yield: 98.30 mole %) of m-xylene diisocyanate having a purity of 98.10% containing 0.1 weight % of m-chloromethyl benzyl isocyanate (hereinafter simply referred to as CBi). The conversion rate of hydrochloride was 99.62%. The results are shown in Table 1 to 3.

Example 2

The same reactor as in Example 1 was used. To the reactor was fed 846 g of orthodichlorobenzene as a reaction solvent, and to the raw material bath were fed 136.2 g (1.0 mole) of m-xylylene diamine and 621 g of orthodichlorobenzene (total amine concentration: 8.5 weight %). Next, the temperature in the reactor was elevated to 120 degree centigrade and then the internal pressure was regulated by 0.05 MPa higher than the atmospheric pressure. Hydrogen chloride gas started to be fed into the reactor at a rate of 43.8 g/hr from the hydrogen chloride gas inlet tube and m-xylylene diamine diluted with a solvent simultaneously started to be fed at a rate of 379 g/hr from the raw material bath by using the raw material feeding pump. The total amount was fed over 2 hours. Furthermore, hydrogen chloride gas was fed at a rate of 20 g/hr and matured for 1 hour. After the completion of the reaction, the conversion rate of the raw material amine was calculated by the neutralization titrimetric method and as a result, the conversion rate was 99.75 mole %. Further, the viscosity of the obtained hydrochloride slurry was measured at 120 degree centigrade using a Brookfield LVT viscometer and as a result, it was 215 mPa·s. So, the slurry had sufficient fluidity. Moreover, a particle diameter of the hydrochloride was measured by using SALD-2100, a laser diffraction particle size analyzer, manufactured by Shimadzu Corporation in an acetonitrile solvent and as a result, the number average particle diameter of the hydrochloride particle was 29 μm. The obtained hydrochloride slurry was in a liquid phase and excellent in the fluidity. So, it was confirmed that when the hydrochloride was transferred to the next step, the hydrochloride did not remain in the reactor and the liquid transfer property was excellent accordingly.

Subsequently, the hydrochloride slurry in the reactor was heated to 160 degree centigrade and then phosgene was blown at a rate of 100 g/hr (1.0 mole/hr) from the phosgene inlet tube. The reaction was carried out for 8 hours while maintaining the temperature. After the completion of the reaction, nitrogen in the system was purged to remove unreacted phosgene and hydrogen chloride gas. The reaction solution was filtered to remove 0.6 g (dry weight) of unreacted hydrochloride. The obtained filtrate was desolvated to obtain 190.3 g (purity conversion yield: 98.50 mole %) of m-xylene diisocyanate having a purity of 97.40% containing 0.3 weight % of CBi. The conversion rate of hydrochloride was 99.70 mole %. The results are shown in Table 1 to 3.

Example 3

The same reactor as in Example 1 was used. To the reactor was fed 846 g of orthodichlorobenzene as a reaction solvent, and to the raw material bath were fed 136.2 g (1.0 mole) of m-xylylene diamine and 621 g of orthodichlorobenzene (total amine concentration: 8.5 weight %). Next, the temperature in the reactor was elevated to 120 degree centigrade and then the internal pressure was regulated by 0.1 MPa higher than the atmospheric pressure. Hydrogen chloride gas started to be fed at a rate of 43.8 g/hr from the hydrogen chloride gas inlet tube and m-xylylene diamine diluted with a solvent simultaneously started to be fed at a rate of 379 g/hr from the raw material bath by using the raw material feeding pump. The total amount was fed over 2 hours. Furthermore, hydrogen chloride gas was fed at a rate of 20 g/hr and matured for 1 hour. After the completion of the reaction, the conversion rate of the raw material amine was calculated by the neutralization titrimetric method and as a result, the conversion rate was 99.81 mole %. Further, the viscosity of the hydrochloride slurry was measured at 120 degree centigrade using a Brookfield LVT viscometer and as a result, it was 221 mPa·s. So, the slurry had sufficient fluidity. Moreover, a particle diameter of the hydrochloride was measured by using SALD-2100, a laser diffraction particle size analyzer, manufactured by Shimadzu Corporation in an acetonitrile solvent and as a result, the number average particle diameter of the hydrochloride particle was 31 μm. The obtained hydrochloride slurry was in a liquid phase and excellent in the fluidity. So, it was confirmed that when the hydrochloride was transferred to the next step, the hydrochloride did not remain in the reactor and the liquid transfer property was excellent accordingly.

Subsequently, the hydrochloride slurry in the reactor was heated to 160 degree centigrade and then phosgene was blown at a rate of 100 g/hr (1.0 mole/hr) from the phosgene inlet tube. The reaction was carried out for 8 hours while maintaining the temperature. After the completion of the reaction, nitrogen in the system was purged to remove unreacted phosgene and hydrogen chloride gas. The reaction solution was filtered to remove 0.4 g (dry weight) of unreacted hydrochloride. The obtained filtrate was desolvated to obtain 188.9 g (purity conversion yield: 98.80 mole %) of m-xylene diisocyanate having a purity of 98.42% containing 0.2 weight % of CBi. The conversion rate of hydrochloride was 99.80 mole %. The results are shown in Table 1 to 3.

Example 4

The same reactor as in Example 1 was used. To the reactor was fed 958 g of orthodichlorobenzene as a reaction solvent, and to the raw material bath were fed 154.2 g (1.0 mole) of bis(aminomethyl)norbornene and 702 g of orthodichlorobenzene (total amine concentration: 8.5 weight %). Next, the temperature in the reactor was elevated to 120 degree centigrade and then the pressure inside the autoclave was regulated by 0.01 MPa higher than the atmospheric pressure. Hydrogen chloride gas started to be fed into the reactor at a rate of 43.8 g/hr from the hydrogen chloride gas inlet tube and bis(aminomethyl)norbornene diluted with a solvent simultaneously started to be fed at a rate of 428.1 g/hr from the raw material bath by using the raw material feeding pump. The total amount was fed over 2 hours. Furthermore, hydrogen chloride gas was fed at a rate of 20 g/hr and matured for 1 hour. After the completion of the reaction, the conversion rate of the raw material amine was calculated by the neutralization titrimetric method and as a result, the conversion rate was 99.88 mole %. Further, the viscosity of the obtained hydrochloride slurry was measured at 120 degree centigrade using a Brookfield LVT viscometer and as a result, it was 241 mPa·s. So, the slurry had sufficient fluidity. Moreover, a particle diameter of the hydrochloride was measured by using SALD-2100, a laser diffraction particle size analyzer, manufactured by Shimadzu Corporation in an acetonitrile solvent and as a result, the number average particle diameter of the hydrochloride particle was 29 μm. The obtained hydrochloride slurry was in a liquid phase and excellent in the fluidity. So, it was confirmed that when the hydrochloride was transferred to the next step, the hydrochloride did not remain in the reactor and the liquid transfer property was excellent accordingly.

Subsequently, the hydrochloride slurry in the reactor was heated to 160 degree centigrade and then phosgene was blown at a rate of 100 g/hr (1.0 mole/hr) from the phosgene inlet tube. The reaction was carried out for 8 hours while maintaining the temperature. After the completion of the reaction, nitrogen in the system was purged to remove unreacted phosgene and hydrogen chloride gas. The reaction solution was filtered to remove 0.5 g (dry weight) of unreacted hydrochloride. The obtained filtrate was desolvated to obtain 206.9 g (purity conversion yield: 98.81 mole %) of bis(isocyanatomethyl)norbornene having a purity of 98.5% containing 0.2 weight % of chloromethyl-isocyanatomethyl norbornene (hereinafter simply referred to as CNi). The conversion rate of hydrochloride was 99.79 mole %. The results are shown in Table 1 to 3.

Example 5

The same reactor as in Example 1 was used. To the reactor was fed 958 g of orthodichlorobenzene as a reaction solvent, and to the raw material bath were fed 154.2 g (1.0 mole) of bis(aminomethyl)norbornene and 702 g of orthodichlorobenzene (total amine concentration: 8.5 weight %). Next, the temperature in the reactor was elevated to 120 degree centigrade and then the internal pressure was regulated by 0.03 MPa higher than the atmospheric pressure. Hydrogen chloride gas started to be fed at a rate of 43.8 g/hr from the hydrogen chloride gas inlet tube and bis(aminomethyl)norbornene diluted with a solvent simultaneously started to be fed at a rate of 428.1 g/hr from the raw material bath by using the raw material feeding pump. The total amount was fed over 2 hours. Furthermore, hydrogen chloride gas was fed at a rate of 20 g/hr and matured for 1 hour. After the completion of the reaction, the conversion rate of the raw material amine was calculated by the neutralization titrimetric method and as a result, the conversion rate was 99.91 mole %. The viscosity of the hydrochloride was measured at 120 degree centigrade using a Brookfield LVT viscometer and as a result, it was 196 mPa·s. So, the hydrochloride had sufficient fluidity. Moreover, a particle diameter of the hydrochloride was measured by using SALD-2100, a laser diffraction particle size analyzer, manufactured by Shimadzu Corporation in an acetonitrile solvent and as a result, the number average particle diameter of the hydrochloride particle was 33 μm. The obtained hydrochloride slurry was in a liquid phase and excellent in the fluidity. So, it was confirmed that when the hydrochloride was transferred to the next step, the hydrochloride did not remain in the reactor and the liquid transfer property was excellent accordingly.

Subsequently, the hydrochloride slurry in the reactor was heated to 160 degree centigrade and then phosgene was blown at a rate of 100 g/hr (1.0 mole/hr) from the phosgene inlet tube. The reaction was carried out for 8 hours while maintaining the temperature. After the completion of the reaction, nitrogen in the system was purged to remove unreacted phosgene and hydrogen chloride gas. The reaction solution was filtered to remove 0.5 g (dry weight) of unreacted hydrochloride. The obtained filtrate was desolvated to obtain 206.3 g (purity conversion yield: 98.32 mole %) of bis(isocyanatomethyl)norbornene having a purity of 98.3% containing 0.1 weight % of CNi. The conversion rate of hydrochloride was 99.78 mole %. The results are shown in Table 1 to 3.

Example 6

The same reactor as in Example 1 was used. To the reactor was fed 566.8 g of orthodichlorobenzene as a reaction solvent, and to the raw material bath were fed 142.2 g (1.0 mole) of bis(aminomethyl)cyclohexane and 476.0 g of o-dichlorochlorobenzene (total amine concentration: 8.5 weight %). Next, the temperature in the reactor was elevated to 120 degree centigrade and then the internal pressure was regulated by 0.01 MPa higher than the atmospheric pressure. Hydrogen chloride gas started to be fed at a rate of 43.8 g/hr from the hydrogen chloride gas inlet tube and amine diluted with a solvent simultaneously started to be fed at a rate of 309.1 g/hr from the raw material bath by using the raw material feeding pump. The total amount was fed over 2 hours. Furthermore, hydrogen chloride gas was fed at a rate of 20 g/hr and matured for 1 hour. After the completion of the reaction, the conversion rate of the raw material amine was calculated by the neutralization titrimetric method and as a result, the conversion rate was 99.88 mole %. The viscosity of the hydrochloride was measured at 120 degree centigrade using a Brookfield LVT viscometer and as a result, it was 213 mPa·s. So, the hydrochloride had sufficient fluidity. Moreover, a particle diameter of the hydrochloride was measured by using SALD-2100, a laser diffraction particle size analyzer, manufactured by Shimadzu Corporation in an acetonitrile solvent and as a result, the number average particle diameter of the hydrochloride particle was 32 μm. The obtained hydrochloride slurry was in a liquid phase and excellent in the fluidity. So, it was confirmed that when the hydrochloride was transferred to the next step, the hydrochloride did not remain in the reactor and the liquid transfer property was excellent accordingly.

Subsequently, the hydrochloride slurry in the reactor was heated to 160 degree centigrade and then phosgene was blown at a rate of 100 g/hr (1.0 mole/hr) from the phosgene inlet tube. The reaction was carried out for 8 hours while maintaining the temperature. After the completion of the reaction, nitrogen in the system was purged to remove unreacted phosgene and hydrogen chloride gas. The reaction solution was filtered to remove 0.4 g (dry weight) of unreacted hydrochloride. The obtained filtrate was desolvated to obtain 194.0 g (purity conversion yield: 98.60 mole %) of bis(isocyanatomethyl)cyclohexane having a purity of 98.70% containing 0.2 weight % of chloromethyl-isocyanatomethyl cyclohexane (hereinafter simply referred to as CHi). The conversion rate of hydrochloride was 99.81%. The results are shown in Table 1 to 3.

Example 7

The same reactor as in Example 1 was used. To the reactor was fed 614.6 g of orthodichlorobenzene as a reaction solvent, and to the raw material bath were fed 154.2 g (1.0 mole) of bis(aminomethyl)norbornene and 516.2 g of orthodichlorobenzene (total amine concentration: 12.0 weight %). Next, the temperature in the reactor was elevated to 120 degree centigrade and then the internal pressure was regulated by 0.01 MPa higher than the atmospheric pressure. Hydrogen chloride gas started to be fed at a rate of 43.8 g/hr from the hydrogen chloride gas inlet tube and bis(aminomethyl)norbornene diluted with a solvent simultaneously started to be fed at a rate of 335.2 g/hr from the raw material bath by using the raw material feeding pump. The total amount was fed over 2 hours. Furthermore, hydrogen chloride gas was fed at a rate of 20 g/hr and matured for 1 hour. After the completion of the reaction, the conversion rate of the raw material amine was calculated by the neutralization titrimetric method and as a result, the conversion rate was 99.86 mole %. The viscosity of the hydrochloride was measured at 120 degree centigrade using a Brookfield LVT viscometer and as a result, it was 1,110 mPa·s. So, the hydrochloride had sufficient fluidity. Moreover, a particle diameter of the hydrochloride was measured by using SALD-2100, a laser diffraction particle size analyzer, manufactured by Shimadzu Corporation in an acetonitrile solvent and as a result, the number average particle diameter of the hydrochloride particle was 35 μm. The obtained hydrochloride slurry was in a liquid phase and excellent in the fluidity. So, it was confirmed that when the hydrochloride was transferred to the next step, the hydrochloride did not remain in the reactor and the liquid transfer property was excellent accordingly.

Subsequently, the hydrochloride slurry in the reactor was heated to 160 degree centigrade and then phosgene was blown at a rate of 100 g/hr (1.0 mole/hr) from the phosgene inlet tube. The reaction was carried out for 8 hours while maintaining the temperature. After the completion of the reaction, nitrogen in the system was purged to remove unreacted phosgene and hydrogen chloride gas. The reaction solution was filtered to remove 0.7 g (dry weight) of unreacted hydrochloride. The obtained filtrate was desolvated to obtain 205.4 g (purity conversion yield: 98.00 mole %) of bis(isocyanatomethyl)norbornene having a purity of 98.4% containing 0.1 weight % of CNi. The conversion rate of hydrochloride was 99.69 mole %. The results are shown in Table 1 to 3.

Example 8

A reactor for obtaining hydrochloride (tank reactor) equipped with a stirrer, a reflux condenser, a thermometer, a hydrogen chloride gas inlet tube, a raw material bath, a raw material feeding pump, a fluidic pump and a pressure regulator was used. In the reactor for obtaining hydrochloride, a value of a diameter of the stirring blade (D1)/an internal diameter of the reaction vessel (D2) was 0.53, a value of the bath diameter (D)/the bath length (L) was 0.73, and a volume of the reaction vessel was 4 m³. The reactor for obtaining hydrochloride was filled with 2,000 kg of orthodichlorobenzene which is a reaction solvent. Next, the temperature in the reactor for obtaining hydrochloride was elevated to 120 degree centigrade and the internal pressure was regulated by 0.1 MPa higher than the atmospheric pressure. Hydrogen chloride gas started to be fed into the reactor for obtaining hydrochloride at a rate of 172 kg/hr from the hydrogen chloride gas inlet tube, and m-xylylene diamine at a rate of 193 kg/hr (1.42 kmole/hr) and orthodichlorobenzene at a rate of 2,078 kg/hr were continuously fed from the raw material bath (total amine concentration: 8.5 weight %). The hydrochloride slurry kept in the reactor for obtaining hydrochloride for 1 hour was continuously flowed into a relay bath equipped with a stirrer and matured for 6 hours. After maturing, the conversion rate of the raw material amine was calculated by the neutralization titrimetric method and as a result, the conversion rate was 99.83 mole %. The viscosity of the hydrochloride slurry was measured at 120 degree centigrade using a Brookfield LVT viscometer and as a result, it was 900 mPa·s. So, the slurry had sufficient fluidity. Moreover, a particle diameter of the hydrochloride was measured by using SALD-2100, a laser diffraction particle size analyzer, manufactured by Shimadzu Corporation in an acetonitrile solvent and as a result, the number average particle diameter of the hydrochloride particle was 33 μm. The obtained hydrochloride slurry was in a liquid phase and excellent in the fluidity. So, when the hydrochloride was transferred to the next step, the hydrochloride did not remain in the reactor and the liquid transfer property was excellent accordingly.

Subsequently, the hydrochloride slurry transferred from the relay bath was heated to 160 degree centigrade in the reactor (phosgenation vessel) and then phosgene was blown at a rate of 1,129 kg/hr (11.4 kmole/hr) from the phosgene inlet tube. The reaction was carried out for 6 hours while maintaining the temperature. After the completion of the reaction, nitrogen in the system was purged to remove unreacted phosgene and hydrogen chloride gas. The reaction solution was filtered to remove 3.6 kg (dry weight) of unreacted hydrochloride. The obtained filtrate was desolvated to obtain 1,603 kg (purity conversion yield: 98.50 mole %) of m-xylene diisocyanate having a purity of 98.3% containing 0.4 weight % of CBi. The conversion rate of hydrochloride was 99.80 mole %. The results are shown in Table 1 to 3.

Example 9

The same reactor for obtaining hydrochloride (tank reactor) as in Example 8 was used. The reactor for obtaining hydrochloride was filled with 2,000 kg of orthodichlorobenzene that is a reaction solvent, and then the temperature in the reactor for obtaining hydrochloride was elevated to 120 degree centigrade and the internal pressure was regulated by 0.05 MPa higher than the atmospheric pressure. Hydrogen chloride gas started to be fed at a rate of 172 kg/hr from the hydrogen chloride gas inlet tube and m-xylylene diamine at a rate of 193 kg/hr (1.42 kmole/hr) and orthodichlorobenzene at a rate of 2,078 kg/hr were continuously fed from the raw material bath (total amine concentration: 8.5 weight %). The hydrochloride slurry kept in the reactor for obtaining hydrochloride for 1 hour was continuously flowed into a relay bath equipped with a stirrer and matured for 6 hours. After maturing, the conversion rate of the raw material amine was calculated by the neutralization titrimetric method and as a result, the conversion rate was 99.47 mole %. The viscosity of the hydrochloride was measured at 120 degree centigrade using a Brookfield LVT viscometer and as a result, it was 1,400 mPa·s. So, the hydrochloride had sufficient fluidity. Moreover, a particle diameter of the hydrochloride was measured by using SALD-2100, a laser diffraction particle size analyzer, manufactured by Shimadzu Corporation in an acetonitrile solvent and as a result, the number average particle diameter of the hydrochloride particle was 38 μm. The obtained hydrochloride slurry was in a liquid phase and excellent in the fluidity. So, when the hydrochloride was transferred to the next step, the hydrochloride did not remain in the reactor and the liquid transfer property was excellent accordingly.

Subsequently, the hydrochloride slurry transferred from the relay bath was heated to 160 degree centigrade in the reactor (phosgenation vessel) and then phosgene was blown at a rate of 1,129 kg/hr (11.4 kmole/hr) from the phosgene inlet tube. The reaction was carried out for 6 hours while maintaining the temperature. After the completion of the reaction, nitrogen in the system was purged to remove unreacted phosgene and hydrogen chloride gas. The reaction solution was filtered to remove 5.2 kg (dry weight) of unreacted hydrochloride. The obtained filtrate was desolvated to obtain 1,607 kg (purity conversion yield: 98.30 mole %) of m-xylene diisocyanate having a purity of 97.9% containing 0.5 weight % of CBi. The conversion rate of hydrochloride was 99.70 mole %. The results are shown in Table 1 to 3.

Comparative Example 1

An autoclave (reactor) equipped with a reflux condenser, a stirring blade, a thermometer, a hydrogen chloride gas inlet tube, a phosgene inlet tube, a raw material bath and a raw material feeding pump was used. In the reactor, a value of a diameter of the stirring blade (D1)/an internal diameter of the reaction vessel (D2) was 0.7, a value of the bath diameter (D)/the bath length (L) was 0.59, and an inner volume of the reaction vessel was 2 L. To the reactor was fed 846 g of orthodichlorobenzene as a reaction solvent, and to the raw material bath were fed 136.2 g (1.0 mole) of m-xylylene diamine and 621 g of orthodichlorobenzene (total amine concentration: 8.5 weight %). Next, under the atmospheric pressure, the temperature in the reactor was elevated to 120 degree centigrade. Thereafter, hydrogen chloride gas started to be fed at a rate of 43.8 g/hr from the hydrogen chloride gas inlet tube and amine diluted with a solvent simultaneously started to be fed at a rate of 379 g/hr from the raw material bath by using the raw material feeding pump. The total amount was fed over 2 hours. Furthermore, hydrogen chloride gas was fed at a rate of 20 g/hr and matured for 1 hour. After the completion of the reaction, the conversion rate of the raw material amine was calculated by the neutralization titrimetric method and as a result, the conversion rate was 97.81 mole %. The viscosity of the hydrochloride was measured at 120 degree centigrade using a Brookfield LVT viscometer and as a result, it was 3,320 mPa·s, exhibiting a whip shape. The obtained hydrochloride slurry was viscous and poor in the fluidity. So, it was confirmed that when the hydrochloride was transferred to the next step, the hydrochloride remained in the reactor in large quantities and the liquid transfer property was bad accordingly. Moreover, a particle diameter of the hydrochloride was measured by using SALD-2100, a laser diffraction particle size analyzer, manufactured by Shimadzu Corporation in an acetonitrile solvent and as a result, the number average particle diameter of the hydrochloride particle was 100 μm.

Subsequently, the hydrochloride slurry in the reactor was heated to 160 degree centigrade and then phosgene was blown at a rate of 100 g/hr (1.0 mole/hr) from the phosgene inlet tube. The reaction was carried out for 8 hours while maintaining the temperature. After the completion of the reaction, nitrogen in the system was purged to remove unreacted phosgene and hydrogen chloride gas. The reaction solution was filtered to remove 8.2 g (dry weight) of unreacted hydrochloride by filtering. The obtained filtrate was desolvated to obtain 183.3 g (purity conversion yield: 93.71 mole %) of m-xylene diisocyanate having a purity of 96.20% containing 1.1 weight % of CBi. The conversion rate of hydrochloride was 96.10 mole %. The results are shown in Table 1 to 3.

Comparative Example 2

The same reactor as in Comparative Example 1 was used. To the reactor was fed 958 g of orthodichlorobenzene as a reaction solvent, and to the raw material bath were fed 154.2 g (1.0 mole) of bis(aminomethyl)norbornene and 702 g of orthodichlorobenzene (total amine concentration: 8.5 weight %). Next, under the atmospheric pressure, the temperature in the reactor was elevated to 100 degree centigrade. Thereafter, hydrogen chloride gas started to be fed at a rate of 43.8 g/hr from the hydrogen chloride gas inlet tube and amine diluted with a solvent simultaneously started to be fed at a rate of 428.1 g/hr from the raw material bath by using the raw material feeding pump. The total amount was fed over 2 hours. Furthermore, hydrogen chloride gas was fed at a rate of 20 g/hr and matured for 1 hour. After the completion of the reaction, the conversion rate of the raw material amine was calculated by the neutralization titrimetric method and as a result, the conversion rate was 98.10 mole %. The viscosity of the hydrochloride was measured at 120 degree centigrade using a Brookfield LVT viscometer and as a result, it was 5,180 mPa·s, exhibiting a whip shape. The obtained hydrochloride slurry was viscous and poor in the fluidity. So, it was confirmed that when the hydrochloride was transferred to the next step, the hydrochloride remained in the reactor in large quantities and the liquid transfer property was bad accordingly. Moreover, a particle diameter of the hydrochloride was measured by using SALD-2100, a laser diffraction particle size analyzer, manufactured by Shimadzu Corporation in an acetonitrile solvent and as a result, the number average particle diameter of the hydrochloride particle was 150 μm.

Subsequently, the hydrochloride slurry in the reactor was heated to 160 degree centigrade and then phosgene was blown at a rate of 100 g/hr (1.0 mole/hr) from the phosgene inlet tube. The reaction was carried out for 8 hours while maintaining the temperature. After the completion of the reaction, nitrogen in the system was purged to remove unreacted phosgene and hydrogen chloride gas. The reaction solution was filtered to remove 7.9 g (dry weight) of unreacted hydrochloride. The obtained filtrate was desolvated to obtain 200.9 g (purity conversion yield: 93.51 mole %) of bis(isocyanatomethyl)norbornene having a purity of 96.00% containing 0.9 weight % of CNi. The conversion rate of hydrochloride was 96.52%. The results are shown in Table 1 to 3.

Comparative Example 3

The same reactor as in Comparative Example 1 was used. To the reactor was fed 883 g of orthodichlorobenzene as a reaction solvent, and to the raw material bath were fed 142.2 g (1.0 mole) of bis(aminomethyl)cyclohexane and 647.8 g of orthodichlorobenzene (total amine concentration: 8.5 weight %). Next, under the atmospheric pressure, the temperature in the reactor was elevated to 100 degree centigrade. Thereafter, hydrogen chloride gas started to be fed at a rate of 43.8 g/hr from the hydrogen chloride gas inlet tube and amine diluted with a solvent simultaneously started to be fed at a rate of 395 g/hr from the raw material bath by using the raw material feeding pump. The total amount was fed over 2 hours. Furthermore, hydrogen chloride gas was fed at a rate of 20 g/hr and matured for 1 hour. After the completion of the reaction, the conversion rate of the raw material amine was calculated by the neutralization titrimetric method and as a result, the conversion rate was 97.85 mole %. The viscosity of the hydrochloride was measured at 120 degree centigrade using a Brookfield LVT viscometer and as a result, it was 4,100 mPa·s, exhibiting a whip shape. The obtained hydrochloride slurry was viscous and poor in the fluidity. So, it was confirmed that when the hydrochloride was transferred to the next step, the hydrochloride remained in the reactor in large quantities and the liquid transfer property was bad accordingly. Moreover, a particle diameter of the hydrochloride was measured by using SALD-2100, a laser diffraction particle size analyzer, manufactured by Shimadzu Corporation in an acetonitrile solvent and as a result, the number average particle diameter of the hydrochloride particle was 120 μm.

Subsequently, the hydrochloride slurry in the reactor was heated to 160 degree centigrade and then phosgene was blown at a rate of 100 g/hr (1.0 mole/hr) from the phosgene inlet tube. The reaction was carried out for 8 hours while maintaining the temperature. After the completion of the reaction, nitrogen in the system was purged to remove unreacted phosgene and hydrogen chloride gas. The reaction solution was filtered to remove 8.8 g (dry weight) of unreacted hydrochloride by filtering. The obtained filtrate was desolvated to obtain 188.0 g (purity conversion yield: 94.09 mole %) of bis(isocyanatomethyl)cyclohexane having a purity of 97.20% containing 1.0 weight % of CHi. The conversion rate of hydrochloride was 95.91%. The results are shown in Table 1 to 3.

Comparative Example 4

The same reactor as in Comparative Example 1 was used. To the reactor was fed 958 g of orthodichlorobenzene as a reaction solvent, and to the raw material bath were fed 154.2 g (1.0 mole) of bis(aminomethyl)norbornene and 702 g of orthodichlorobenzene (total amine concentration: 8.5 weight %). Next, the temperature in the reactor was elevated to 100 degree centigrade and then the internal pressure was regulated by 0.001 MPa higher than the atmospheric pressure. Hydrogen chloride gas started to be fed at a rate of 43.8 g/hr from the hydrogen chloride gas inlet tube and amine diluted with a solvent simultaneously started to be fed at a rate of 428.1 g/hr from the raw material bath by using the raw material feeding pump. The total amount was fed over 2 hours. Furthermore, hydrogen chloride gas was fed at a rate of 20 g/hr and matured for 1 hour. After the completion of the reaction, the conversion rate of the raw material amine was calculated by the neutralization titrimetric method and as a result, the conversion rate was 98.90 mole %. The viscosity of the hydrochloride was measured at 120 degree centigrade using a Brookfield LVT viscometer and as a result, it was 3,180 mPa·s, exhibiting a whip shape. The obtained hydrochloride slurry was viscous and poor in the fluidity. So, it was confirmed that when the hydrochloride was transferred to the next step, the hydrochloride remained in the reactor in large quantities and the liquid transfer property was bad accordingly. Moreover, a particle diameter of the hydrochloride was measured by using SALD-2100, a laser diffraction particle size analyzer, manufactured by Shimadzu Corporation in an acetonitrile solvent and as a result, the number average particle diameter of the hydrochloride particle was 80 μm.

Subsequently, the hydrochloride slurry in the reactor was heated to 160 degree centigrade and then phosgene was blown at a rate of 100 g/hr (1.0 mole/hr) from the phosgene inlet tube. The reaction was carried out for 8 hours while maintaining the temperature. After the completion of the reaction, nitrogen in the system was purged to remove unreacted phosgene and hydrogen chloride gas. The reaction solution was filtered to remove 5.9 g (dry weight) of unreacted hydrochloride. The obtained filtrate was desolvated to obtain 202.0 g (purity conversion yield: 94.51 mole %) of bis(isocyanatomethyl)norbornene having a purity of 96.50% containing 0.9 weight % of CNi. The conversion rate of hydrochloride was 97.40%. The results are shown in Table 1 to 3.

TABLE 1

| | Raw Material Amine Species | Reaction Solvent | Pressure * (MPa) | Concentration of Raw Material Amine (weight %) |
|---|---|---|---|---|
| Example 1 | XDA | ODCB | 0.01 | 8.5 |
| Example 2 | XDA | ODCB | 0.05 | 8.5 |
| Example 3 | XDA | ODCB | 0.1 | 8.5 |
| Example 4 | NBDA | ODCB | 0.01 | 8.5 |
| Example 5 | NBDA | ODCB | 0.03 | 8.5 |
| Example 6 | H6XDA | ODCB | 0.01 | 8.5 |
| Example 7 | NBDA | ODCB | 0.01 | 12 |
| Example 8 | XDA | ODCB | 0.1 | 8.5 |
| Example 9 | XDA | ODCB | 0.05 | 8.5 |
| Comparative Example 1 | XDA | ODCB | Atmospheric pressure | 8.5 |
| Comparative Example 2 | NBDA | ODCB | Atmospheric pressure | 8.5 |
| Comparative Example 3 | H6XDA | ODCB | Atmospheric pressure | 8.5 |
| Comparative Example 4 | NBDA | ODCB | 0.001 | 8.5 |

* "Pressure" is the internal pressure in reaction for obtaining hydrochloride.

TABLE 2

| | Conversion Rate of Raw Material Amine (mole %) | Viscosity of Hydrochloride (mpa·s) | Fluidity of Hydrochloride Slurry | Liquid Transfer Property of Hydrochloride Slurry | Particle Diameter of Hydrochloride (μm) |
|---|---|---|---|---|---|
| Example 1 | 99.80 | 201 | Good | Good | 25 |
| Example 2 | 99.75 | 215 | Good | Good | 29 |
| Example 3 | 99.81 | 221 | Good | Good | 31 |
| Example 4 | 99.88 | 241 | Good | Good | 29 |
| Example 5 | 99.91 | 196 | Good | Good | 33 |
| Example 6 | 99.88 | 213 | Good | Good | 32 |
| Example 7 | 99.86 | 1110 | Good | Good | 35 |
| Example 8 | 99.83 | 900 | Good | Good | 33 |

TABLE 2-continued

|  | Conversion Rate of Raw Material Amine (mole %) | Viscosity of Hydrochloride (mpa·s) | Fluidity of Hydrochloride Slurry | Liquid Transfer Property of Hydrochloride Slurry | Particle Diameter of Hydrochloride (μm) |
|---|---|---|---|---|---|
| Example 9 | 99.47 | 1400 | Good | Good | 38 |
| Comparative Example 1 | 97.81 | 3320 | Bad | Bad | 100 |
| Comparative Example 2 | 98.10 | 5180 | Bad | Bad | 150 |
| Comparative Example 3 | 97.85 | 4100 | Bad | Bad | 120 |
| Comparative Example 4 | 98.90 | 3180 | Bad | Bad | 80 |

TABLE 3

|  | Conversion Rate of Hydrochloride (mole %) | Generation Rate of Chloride (weight %) | Purity of Isocyanate (weight %) | Yield of Isocyanate (mole %) |
|---|---|---|---|---|
| Example 1 | 99.62 | 0.1 | 98.10 | 98.30 |
| Example 2 | 99.70 | 0.3 | 97.40 | 98.50 |
| Example 3 | 99.80 | 0.2 | 98.42 | 98.80 |
| Example 4 | 99.79 | 0.2 | 98.50 | 98.81 |
| Example 5 | 99.78 | 0.1 | 98.30 | 98.32 |
| Example 6 | 99.80 | 0.2 | 98.70 | 98.60 |
| Example 7 | 99.69 | 0.1 | 98.40 | 98.00 |
| Example 8 | 99.80 | 0.4 | 98.30 | 98.50 |
| Example 9 | 99.70 | 0.5 | 97.90 | 98.30 |
| Comparative Example 1 | 96.10 | 1.1 | 96.20 | 93.71 |
| Comparative Example 2 | 96.52 | 0.9 | 96.00 | 93.51 |
| Comparative Example 3 | 95.91 | 1.0 | 97.20 | 94.09 |
| Comparative Example 4 | 97.40 | 0.9 | 96.50 | 94.51 |

The invention claimed is:

1. A process for producing a linear or cyclic aliphatic isocyanate comprising a step of reacting an amine compound selected from the group consisting of m-xylylene diamine, bis(aminomethyl)norbornene and bis(aminomethyl)cyclohexane with hydrogen chloride to yield a hydrochloride of the linear or cyclic aliphatic amine, wherein said step is performed under a pressure higher by a range of 0.01 to 0.1 MPa more than atmospheric pressure wherein the amine hydrochloride is reacted with phosgene to produce the linear or cyclic aliphatic isocyanate.

2. The process for producing a linear or cyclic aliphatic isocyanate as set forth in claim 1, wherein said step is a step of reacting the amine compound with hydrogen chloride in an organic solvent in a tank reactor.

3. The process for producing a linear or cyclic aliphatic isocyanate as set forth in claim 1, wherein said step is a step of reacting the amine compound in an organic solvent with hydrogen chloride blown into the organic solvent.

4. The process for producing a linear or cyclic aliphatic isocyanate as set forth in claim 1, wherein the viscosity of a slurry containing the hydrochloride of the amine compound obtained in said step measured at 120 degree centigrade using a Brookfield LVT viscometer is not more than 2,000 mPa·s.

5. The process for producing a linear or cyclic aliphatic isocyanate as set forth in claim 1, wherein the reaction temperature in said step is not less than −20 degree centigrade and not more than 180 degree centigrade.

6. The process for producing a linear or cyclic aliphatic isocyanate as set forth in claim 1, wherein at least one kind of organic aromatic solvent is used in said step.

7. The process for producing a linear or cyclic aliphatic isocyanate as set forth in claim 1, wherein said linear or cyclic aliphatic isocyanate is one or more compounds selected from xylylene diisocyanate, bis(isocyanatomethyl)norbornene and bis(isocyanatomethyl)cyclohexane.

8. The process for producing a linear or cyclic aliphatic isocyanate as set forth in claim 1, wherein the total amine concentration in the reaction system is not less than 5 weight % and not more than 40 weight % in said step.

9. A process for producing a hydrochloride of a linear or cyclic aliphatic amine, which comprises reacting an amine compound selected from the group consisting of m-xylylene diamine, bis(aminomethyl)norbornene and bis(aminomethyl)cyclohexane with hydrogen chloride under a pressure higher by a range of 0.01 to 0.1 MPa more than atmospheric pressure.

10. The process for producing a hydrochloride of a linear or cyclic aliphatic amine as set forth in claim 9, which comprises reacting an amine compound selected from the group consisting of m-xylylene diamine, bis(aminomethyl)norbornene and bis(aminomethyl)cyclohexane with hydrogen chloride in an organic solvent in a tank reactor.

11. The process for producing a hydrochloride of a linear or cyclic aliphatic amine as set forth in claim 9, which comprises reacting an amine compound selected from the group consisting of m-xylylene diamine, bis(aminomethyl)norbornene and bis(aminomethyl)cyclohexane in an organic solvent with hydrogen chloride blown into the organic solvent.

* * * * *